US009040075B2

(12) United States Patent
Auestad et al.

(10) Patent No.: US 9,040,075 B2
(45) Date of Patent: May 26, 2015

(54) METHOD OF INCREASING LEAN BODY MASS AND REDUCING BODY FAT MASS IN INFANTS (75) Inventors: Nancy Auestad, Battle Creek, MI (US); Joan R. Jacobs, San Francisco, CA (US)

(73) Assignee: ABBOTT LABORATORIES, Abbott Park, IL (US)

( * ) Notice: Subject to any disclaimer, the term of this patent is extended or adjusted under 35 U.S.C. 154(b) by 541 days.

(21) Appl. No.: 10/576,522

(22) PCT Filed: Dec. 17, 2004

(86) PCT No.: PCT/US2004/042770
§ 371 (c)(1),
(2), (4) Date: Apr. 19, 2006

(87) PCT Pub. No.: WO2005/063050
PCT Pub. Date: Jul. 14, 2005

(65) Prior Publication Data
US 2007/0026049 A1 Feb. 1, 2007

Related U.S. Application Data (60) Provisional application No. 60/531,495, filed on Dec. 19, 2003.

(51) Int. Cl.
*A61K 47/00* (2006.01)
*A01N 37/00* (2006.01)
*A61K 38/00* (2006.01)
*A23L 1/221* (2006.01)
*A23G 3/00* (2006.01)
*A23C 9/16* (2006.01)
*A23L 1/30* (2006.01)
*A23L 1/29* (2006.01)
*A61K 31/202* (2006.01)

(52) U.S. Cl.
CPC .............. *A23L 1/3008* (2013.01); *A23L 1/293* (2013.01); *A23L 1/296* (2013.01); *A61K 31/202* (2013.01); *A23V 2002/00* (2013.01)

(58) Field of Classification Search
None
See application file for complete search history.

(56) References Cited

U.S. PATENT DOCUMENTS

2002/0018828 A1* 2/2002 Lepine .............................. 426/2
2002/0025983 A1 2/2002 Horrobin
2002/0045660 A1* 4/2002 O'Connor et al. ............ 514/560

FOREIGN PATENT DOCUMENTS

| EP | 231904 A2 * | 8/1987 |
| EP | 0 231 904 B1 | 5/1991 |
| WO | WO 98/44917 | 10/1998 |
| WO | WO 9844917 A1 * | 10/1998 |

OTHER PUBLICATIONS

Innis SM. et al., Docosahexaenoic acid and arachidonic acid enhance growth with no adverse effects in pre-term infants fed formula, J Pediatr. May 2002;140(5):547-54.*
Koletzko B. et al., Physiological Aspects of Human Milk Lipids, Early Hum Dev. Nov. 2001;65 Suppl:S3-S18.*
Berthold Koletzko, Fatty Acids and Early Human Growth, American Journal of Clinical Nutrition, vol. 73, No. 4, 671-672, Apr. 2001.*
JCK Wells, A Hattori chart analysis of body mass index in infants and children, International Journal of Obesity (2000) 24, 325-329.*
Machine Translation of EP 0231904A2, Jan. 1987.*
Carlson SE, Neuringer M. "Polyunsaturated fatty acid status and neurodevelopment: a summary and critical analysis of the literature." Lipids 1999; 34: 171-78.
Innis SM. "The role of dietary n-6 and n-fatty acids in developing brain." Develop Neurosci 2000; 22: 474-80.
O'Connor DL, Hall R, Adamkin D, Auestad N, Castillo M, Connor WE, et al. "Growth and development in preterm infants fed long-chain polyunsaturated fatty acids: a prospective, randomized controlled trial." Pediatrics 2001; 108: 359-71.
SanGiovanni JP, Berkey CS, Dwyer JT, Colditz GA. "Dietary essential fatty acids, long-chain polyunsaturated fatty acids, and visual resolution acuity in healthy fullterm infants: a systematic review." Early Hum Dev 2000; 57:165-88.
Innis SM, Adamkin DH, Hall RT, Kalhan SC, Lair C, Lim M, et al. "Docosahexaenoic acid and arachidonic acid enhance growth with no adverse effects in preterm infants fed formula." J Pediatr 2002; 140:547-54.
Martinez FE, Sieber VM, Jorge SM, Ferlin ML, Mussi-Pinhata MM. "Effect of supplementation of preterm formula with long chain polyunsaturated fatty acids on mineral balance in preterm infants." J Pediatr Gastroenterol Nutr 2002; 35:503-7.
Vanderhoof J, Gross S, Hegyl T. "A multicenter long-term safety and efficacy trial of preterm formula supplemented with long-chain polyunsaturated fatty acids." J Pediatr Gastroenterol Nutr 2000;31:121-27.
Fewtrell MS, Morley R, Abbott RA, Singhal A, Isaacs EB, Stephenson T, et al. Double-blind, randomized trial of long-chain polyunsaturated fatty acid supplementation in fomula fed to preterm infants. Pediatrics 2002;110:73-82.
Watkins BA, Lippman HE, Le Bouteiller L, Li Y, Seifert MF. "Bioactive fatty acids: role in bone biology and bone cell function." Prog Lipid Res 2001; 40:125-48.
Peyron-Case E, Quignard-Boulange A, Laromiguiere M, Feing-Kwong-Chan S, Veronese A, Ardouin B, et al. Dietary fish oil increases lipid mobilization but does not decrease lipid storage-related enzyme activities in adipose tissue of insulin-resistant, sucrose-fed rats. J. Nutr 2003;133:2239-43.

(Continued)

Primary Examiner — Michael G Hartley
Assistant Examiner — Nabila Ebrahim
(74) Attorney, Agent, or Firm — Calfee, Halter & Griswold LLP (57) ABSTRACT

Disclosed is a method of increasing lean body mass and reducing fat body mass in infants, said method comprising administration to an infant, term or preterm, a nutritional formula comprising a source of DHA and ARA. It has been found that the administration of DHA and ARA, or a source thereof, in infants can increase lean body mass and reduce fat body mass, when compared to an unsupplemented control formula, without impacting the total overall growth of the infant. This method is especially useful in preterm infants.

14 Claims, 1 Drawing Sheet

(56) References Cited

OTHER PUBLICATIONS

Raclot T, Groscolas R, Langin D, Ferre P. Site-specific regulation of gene expression by n-3 polyunsaturated fatty acids in rat white adipose tissues. J Lipid Res 1997; 38:1963-72.

Raisz LG. "Bone cell biology: new approaches and unanswered questions." J Bone Miner Res 1993;8:S457-65.

Watkins BA, Li Y, Lippman HE, Feng S. "Modulatory effect of omega-3 polyunsaturated fatty acids on osteoblast function and bone metabolism." Prostaglandins Leukot Essent Fatty Acids 2003;68:387-98.

Association for Official Agricultural Chemists. Official Methods of Analysis. In. 14$^{th}$ ed. Arlington, VA: Association for Official Agricultural Chemists; 1984;28.082-28.085.

Carver JD, Wu PY, Hall RT, Ziegler EE, Sosa R, Jacobs J, et al. "Growth of preterm infants fed nutrient-enriched or term formula after hospital discharge." Pediatrics 2001;107:683-89.

Cooke RJ, Embleton ND, Griffin IJ, Wells JC, McCormick KP. "Feeding preterm infants after hospital discharge: growth and development at 18 months of age." Pediatr Res 2001;49:719-22.

Lucas A, Fewtrell MS, Morley R, Singhal A, Abbott RA, Isaacs E, et al. Randomized trial of nutrient-enriched formula versus standard formula for postdischarge preterm infants. Pediatrics 2001;108:703-11.

Worrell LA, Thorp JW, Tucker R, McKinley LT, Chen J, Chng YM, et al. The effects of the introduction of a high-nutrient transitional formula on growth and development of very-low birth-weight infants. J Perinatol 2002;22:112-19.

Rajaram S, Carlson SE, Koo WW, Braselton WE. "Plasma mineral concentrations in preterm infants fed a nutrient-enriched formula after hospital discharge." J Pediatr 1995;126:791-96.

Bishop NJ, King FJ, Lucas A. "Increased bone mineral content of preterm infants fed with a nutrient enriched formula after discharge from hospital." Arch Dis Child 1993;68:573-78.

Brunton JA, Saigal S, Atkinson SA. "Growth and body composition in infants with bronchopulmonary dysplasia up to 3 months corrected age: a randomized trial of a high-energy nutrient-enriched formula fed after hospital discharge." J Pediatr 1998;133:340-45.

Chan GM. "Growth and bone mineral status of discharged very low birth weight infants fed different formulas or human milk." J. Pediatr 1993;123:439-43.

Cooke RJ, McCormick K, Griffin IJ, Embleton N, Faulkner K, Wells JC, et al. "Feeding preterm infants after hospital discharge: effect of diet on body composition." Pediatr Res 1999;46:461-64.

DeCurtis M, Pieltain C, Rigo J. "Body composition in preterm infants fed standard term or enriched formula after hospital discharge." Eur J Nutr 2002;41:177-82.

Carlson SE, Cooke RJ, Werkman SH, Tolley EA. "First year growth of preterm infants fed standard compared to marine oil n-3 supplemented formula." Lipids 1992;27:901-7.

Carlson SE, Werkman SH, Tolley EA. "Effect of long-chain n-3 fatty acid supplementation on visual acuity and growth of preterm infants with and without bronchopulmonary dysplasia." Am. J. Clin Nutr 1996;63:687-97.

Ryan AS, Montalto MB, Groh-Wargo S, Mimouni F, Sentipal-Walerius J, Doyle J, et al. "Effect of DHA-containing formula on growth of preterm infants to 59 weeks postmenstrual age." Am J Human Biol 1999;11:457-67.

Clandinin MT, Van Aerde JE, Parrott A, Field CJ, Euler AR, Lien EL. "Assessment of the efficaious dose of arachidonic and docosahexaenoic acids in preterm infant formulas: fatty acid composition of erythrocyte membrane lipids." Pediatr Res 1997;42:819-25.

Faldella G, Govoni M, Alexxandroni R, Marchiani E, Salvioli GP, Biagi PL, et al. "Visual evoked potentials and dietary long chain polyunsaturated fatty acids in preterm infants." Arch Dis Child Fetal Neonatal Ed 1996;75:F108-12.

Uauy R, Hoffman DR, Birch EE, Birch DG, Jameson DM, Tyson J. "Safety and efficacy of omega-3 fatty acids in the nutrition of very low birth weight infants: soy oil and marine oil supplementation of formula." J Pediatr 1994;124:612-20.

Vanderhoof J, Gross S, Hegyi T, Clandinin T, Porcelli P, DeCristofaro J, et al. "Evaluation of a long-chain polyunsaturated fatty acid supplemented formula on growth, tolerance and plasma lipids in preterm infants up to 48 weeks postconceptional age." J Pediatr Gastroenterol Nutr 1999;3 18-26.

Wauben IP, Atkinson SA, Shah JK, Paes B. Growth and body composition of preterm infants: Influence of nutrient fortification of mother's milk in hospital and breastfeeding post-hospital discharge. Acta Paediatr 1998;87:780-85.

Schmelze HR, Fusch C. "Body fat in neonates and young infants: validation of skinfold thickness versus dual-energy Z-ray absorptiometry." Am J. Clin Nutr 2002;76:1096-00.

Raclot T, Oudart H. "Selectivity of fatty acids on lipid metabolism and gene expression." Proc Nutr Soc 1999;58:633-46.

Hill JO, Peters JC, Lin D, Yakubu F, Greene J, Swift L. "Lipid accumulation and body fat distribution is influenced by type of dietary fat fed to rats." Int J Obes Relat Metab Disord. 1993; 17:223-36.

Parrish CC, Pathy DA, Angel A. "Dietary fish oils limit adipose tissue hypertrophy in rats." Metabolism 1990;30:217-19.

Petersen RK, Jorgensen C, Rustan AC, Froyland L, Muller-Decker K, Furstenberger G, et al. Arachidonic acid-dependent inhibition of adipocyte differentiation requires PKA activity and is associated with sustained expression of cyclooxygenases. J Lipid Res 2003;16.

Benhizia F, Hainault I, Serougne C, Lagrange D, Hajduch E, Guichard C, et al. "Effects of a fish oil-lard diet on rat plasma lipoproteins, liver FAS, and lipolytic enzymes." Am J Physiol 1994;267:E975-82.

Halvorsen B, Rustan AC, Madsen L, Reseland J, Berge RK, Sletnes P, et al. "Effects of long-chain monounsaturated and n-3 fatty acids on fatty acid oxidation and lipid composition in rats." Ann Nutr Metab 2001;45:30-7.

Rustan AC, Hustvedt BE, Drevon CA. "Postprandial decrease in plasma unesterified fatty acids during n-3 fatty acid feeding is not caused by accumulation of fatty acids in adipose tissue." Biochim Biophys Acta 1998;1390:245-57.

Peyron-Case E, Tavema M, Guerre-Millo M, Veronese A, Pacher N, Slama G, et al. "Dietary (n-3) polyunsaturated fatty acids up-regulate plasma leptin in insulin-resistant rats." J Nutr 2002;132:2235-40.

Lapillonne A, Braillon P, Claris O, Chatelain PG, Delmas PD, Salle BL. "Body composition in appropriate and in small for gestational age infants." Acta Paediatr 1997;86:196-00.

Hediger ML, Overpek MD, Kuczmarski RJ, McGlynn A, Maurer KR, Davis WW. "Muscularity and fatness of infants and young children born small- or large-for-gestational-age." Pediatrics 1998;102:E60.

Barker DJ. "Intrauterine programming of coronary heart disease and stroke." Acta Paediatr Suppl 1997;423:178-82.

Barker DJ. "The fetal origins of coronary heart disease." Acta Paediatr Suppl 1997;422:78-82.

Phipps K, Barker DJ, Hales CN, Fall CH, Osmond C, Clark PM. "Fetal growth and impaired glucose tolerance in men and women." Diabetologia 1993;36:225-28.

Ehrenkraza RA, Younes N, Lemons JA, Fanaroff AA, Donovan EF, Wright LL, et al. "Longitudinal growth of hospitalized very low birth weight infants." Pediatrics 1999;104:280-89.

Koo WW, Hammami M, Margeson DP, Nwaesei C, Montalto MB, Lasekan JB. "Reduced bone mineralization in infants fed palm olein-containing formula: a radmonized, double-blinded, prospective trial." Pediatrics 2003;111:1017-23.

Watkins BA, Li Y, Allen KG, Hoffmann WE, Seifert MF. "Dietary ratio of (n-6/(n-3) polyunsaturated fatty acids alters the fatty acid composition of bone compartments and biomarkers of bone formation in rats." J Nutr 2000;130:2274-84.

Lucia VD, Fitzpatrick-Wong SC, Weiler HA. "Dietary arachidonic acid suppresses bone turnover in contrast to low dosage exogenous prostaglandin E(2) that elevates bone formation in the piglet." Prostaglandins Leukot Essent Fatty Acids 2003;68:407-13.

Weiler H. "Dietary supplementation of arachidonic acid is associated with higher whole body weight and bone mineral density in growing pigs." Pediatr Res 2000;47:692-97.

Watkins BA, Shen CL, Allen KG, Seifert MF. "Dietary (n-3) and (n-6) polyunsaturates and acetylsalicylic acid alter ex vivo PGE2

(56) References Cited

OTHER PUBLICATIONS biosynthesis, tissue IGF-I levels, and bone morphometry in chicks." J Bone Miner Res 1996;11:1321-32.

Watkins BA, Shen CL, McMurtry JP, Xu H, Bain SD, Allen KG, et al. "Dietary lipids modulate bone prostaglandin E2 production, insulin-like growth factor-I concentration and formation rate in chicks." J Nutr 1997;127:1084-91.

Weiler HA, Fitzpatrick-Wong S. "Dietary long-chain polyunsaturated fatty acids minimize dexamethasone-induced reductions in arachidonic acid status but not bone mineral content in piglets." Pediatr Res 2002;51:282-89.

Rigo J, De Curtis M, Pieltain C, Picaud JC, Salle BL, Senterre J. "Bone mineral metabolism in the micropremie." Clin Perinatol 2000;27:147-70.

Koletzko, et al., "Fette in der Ernahrung von Neugeborenen mit Niedrigem Geburtsgewicht," Monatscchrift Fuer Kinderheilkunde, Springer Verlag, vol. 7, Suppl. 2, No. 143, pp. 99-104 (1995).

International Preliminary Report on Patentability for PCT/US04/42770, dated Jun. 20, 2006.

* cited by examiner

METHOD OF INCREASING LEAN BODY MASS AND REDUCING BODY FAT MASS IN INFANTS

CROSS-REFERENCE TO RELATED APPLICATIONS

This application is the U.S. national stage entry of PCT/US2004/042770, with an international filing date of Dec. 17, 2004, which claims the benefit of and priority to U.S. Provisional Patent Application Ser. No. 60/531,495, entitled METHOD OF INCREASING LEAN BODY MASS AND REDUCING BODY FAT MASS IN INFANTS and filed Dec. 19, 2003, the entire disclosures of which are incorporated herein by reference in their entirety, to the extent that it is not conflicting with the present application.

FIELD OF INVENTION

The present invention relates to a method of increasing lean body mass and reducing body fat mass in infants by feeding the infants a nutritional formula containing docosahexaenoic acid (DHA) and arachidonic acid (ARA).

BACKGROUND OF THE INVENTION

Long chain polyunsaturated fatty acids such as docosahexaenoic acid (DHA) and arachidonic acid (ARA) are well known for use in infant nutritional formulas, commercially available examples of which include Similac® Advance® Infant Formula and Isomil® Advance® Infant formula, both of which are available from Ross Products Division, Abbott Laboratories, Columbus, Ohio, USA.

It is well known that ARA and DHA are the predominant long-chain polyunsaturated fatty acids in the central nervous system, and it is believed that an adequate dietary supply during infancy is necessary to support optimum neurodevelopment. For example, numerous investigations have been published which indicate that both visual acuity and neurocognitive development are enhanced in preterm infants fed formulas supplemented with ARA and DHA.

It is also generally known that metabolites of the long-chain polyunsaturated fatty acids (i.e. DHA, ARA and eicosapentaenoic acid [EPA]) are important biomediators that can impact growth and body composition through diverse mechanisms. The levels and ratios of these fatty acids in the diet can influence cell membrane properties, cell-to-cell signaling processes, the expression of genes that regulate cell differentiation and growth, and the synthesis of eicosanoids that affect bone metabolism. Animal studies have been conducted and published which suggest that long-chain polyunsatuated fatty acids in the diet can affect both fat mass, fat distribution, and bone metabolism. There is insufficient information, however, regarding the effects of dietary long-chain polyunsaturated fatty acids, especially ARA and DHA, on body composition in neonatal (infant) animals or in humans.

In studies with adult rodents, for example, diets highly enriched in the long-chain n-3 fatty acids, DHA and EPA, from fish oil with no ARA have been associated with lower body fat when compared with diets rich in saturated fat (e.g., lard, MCT oil) or polyunsaturated fatty acids such as linoleic acid (e.g. corn oil). Other studies with adult rats fed diets similarly enriched in DHA and EPA with no ARA had preferential partitioning of ingested energy toward oxidation at the expense of storage, reduced fat mass, decreased fat cell trophic growth, altered expression of genes involved in adipose tissue metabolism, including lipoprotein lipase activity, increased peroxisomal beta-oxidation, reduced adipocyte cell volumes, increased visceral fat hypertrophy, and altered regulation of leptin.

In a published study of preterm infants fed formulas containing DHA and EPA at less than 0.3% of calories for about five months after hospital discharge, it was noted that infants grew slower and had lower fat-free mass, but fat mass was not different than in infants fed the unsupplemented control formulas Others subsequently found that preterm infants fed formulas containing DHA and EPA and ARA or formulas with DHA and ARA did not have slower growth.

It has now been found, however, that infants fed infant formulas containing DHA and ARA, in contrast to the DHA and EPA (no ARA) enriched animal diets referenced above, had an increased lean body mass and a reduced fat body mass as compared to those fed the control formula, all without an effect on the rate of overall growth of the infants.

It is therefore an object of the present invention to provide a method of providing infant formulas supplemented with ARA and DHA wherein the method provides increased lean body mass and reduced fat mass as compared to a control formula, as applied to both term and preterm infants, without having an impact on overall total growth in the infant.

SUMMARY OF THE INVENTION

The present invention is directed to a method of increasing lean body mass and reducing fat body mass in infants, said method comprising administration to an infant, term or preterm, a nutritional formula comprising a source of DHA and ARA. It has been found that the administration of DHA and ARA, or a suitable source thereof, in infants can increase lean body mass and reduce fat body mass, when compared to an unsupplemented control formula, without having an impact on overall total growth in the infant. This method is especially useful in preterm infants.

DETAILED DESCRIPTION OF THE INVENTION

The method of the present invention comprises the administration to an infant of a nutritional formula containing a source of both DHA and ARA. These and other essential or optional characteristics of the method of the present invention are described in detail hereinafter.

The term "infant" as used herein includes children up to one year corrected age (CA), and includes infants from 0 to about 4 months corrected age, infants from 4 to about 8 months corrected age, infants from about 8 to about 12 months corrected age, low birth weight infants less than 2,500 grams at birth; and premature infants born at less than about 37 weeks gestational age, typically from about 26 weeks to about 34 weeks gestational age.

The term "corrected age" or "CA" as used herein is used to standardize preterm infants to their full term peers for purposes of comparing their growth and development. For example, a preterm infant born 8 weeks prematurely reaches "term corrected age" at approximately 2 months chronological age, and at 6 months chronological age may developmentally be equivalent to a 4 month-old term infant. The "catch-up" goal is to achieve a developmental status more like that of chronological-age peers.

The term "lipid" as used herein, unless otherwise specified, means fats, oils, and combinations thereof.

The terms "infant formula" and "nutritional formula" are used interchangeably herein and refer to nutrition compositions designed for infants, which preferably contain sufficient protein, carbohydrate, lipid, vitamins, minerals, and electrolytes to potentially serve as the sole source of nutrition when provided in sufficient quantities. These formulas, therefore, can be used to provide sole, primary, or supplemental nutrition for the intended infant or infant population.

All percentages, parts and ratios as used herein are by weight of the total composition, unless otherwise specified. All such weights as they pertain to listed ingredients are based on the active level and, therefore, do not include solvents or by-products that may be included in commercially available materials; unless otherwise specified.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be counted as supporting a range of from 2 to 8, from 3 to 7, 5, 6, from 1 to 9, from 3.6 to 4.6, from 3.5 to 9.9, and so forth.

All references to singular characteristics or limitations of the present invention shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The method of the present invention can comprise, consist of or consist essentially of the essential elements and limitations of the invention described herein, as well as any additional or optional ingredients, components, or limitations described herein or otherwise useful in nutrition formula applications.

Arachidonic Acid (ARA) and Docosahexaenoic Acids (DHA)

The method of the present invention comprises the feeding or admission of nutritional formulas to infants, wherein the formulas comprise a combination of arachidonic acid (ARA) and docosahexaenoic acid (DHA).

Arachidonic acid (ARA) and docosahexaenoic acid (DHA) for use in the method of the present invention can be provided by any source suitable for use in an infant formula Arachidonic acid is an organic carboxylic acid having a chain length of 20 carbons and 4 double bonds beginning at the sixth carbon (20:4 n-6). Docosahexaenoic acid is likewise an organic carboxylic acid but has a chain length of 22 carbons with 6 double bonds beginning with the third carbon from the methyl end (22:6 n-3). Non-limiting sources of ARA and DHA include fish oil (providing DHA and EPA), egg derived oils (providing ARA and DHA), fungal oil (providing ARA), algal oil (providing DHA), and combinations thereof.

The concentration or amount of DHA and ARA in the formulas for use in the method of the present invention includes any quantity known for or otherwise suitable for use in infant formulas, embodiments of which are described the following table.

TABLE 1

DHA and ARA Content in Infant Formulas according to the Method herein*

|  | 1$^{st}$ embodiment | 2$^{nd}$ embodiment | 3$^{rd}$ embodiment |
| --- | --- | --- | --- |
|  | Percent total fatty acids in formula (wt/wt) | | |
| ARA | 0.2-1.0 | 0.35-0.7 | 0.4-0.5 |
| DHA | 0.1-1.0 | 0.1-.36 | 0.1-0.3 |
|  | Fatty acid mg/100 kcal formula | | |
| ARA | 10-50 | 18-36 | 20-25 |
| DHA | 3-50 | 5-20 | 5-15 |

*all numerial values preferably modified by the term "about"

The level of DHA and ARA in the formula for use in the method of the present invention can be expressed as in Table 1 as either a percentage of the total fatty acids in the formula or as an amount (mg) of fatty acid per 100 kcal of formula. For percentage of the total fatty acids in the formula, this percentage is multiplied by the absolute concentration of total fatty acids in the formula (either as g/L or g/100 kcal) to provide the absolute concentration of the fatty acid of interest in the formula (in g/L or g/100 kcal, respectively). Total fatty acid content is estimated as being about 95% of the total fat, to thus account for the weight of the glycerol backbone. Conversion from mg/100 kcal to mg/L is a simple calculation dependent upon the caloric density as is known to those skilled in the art for any particular formula.

Daily intake of DHA and ARA in accordance with the method herein can vary depending upon the age and the particular nutritional needs of the infant. Daily DHA intake in accordance with the method generally ranges from about 2 to about 65 mg/kg body weight/day, including from about 3 to about 35 mg/kg body weight/day, and also including from about 7 to about 26 mg/kg body weight/day, whereas daily ARA intake in accordance with the method—generally ranges from about from about 2 to about 65 mg/kg body weight/day, including from about 5 to about 50 mg/kg body weight/day, and also including from about 20 to about 40 mg/kg body weight/day.

The infant formulas for use in the method of the present invention may further comprise many other fatty acid materials and sources thereof in addition to the requisite ARA and DHA components described herein, provided that all such additional materials are stable for use in an infant nutritional formula. Non-limiting examples of such additional fatty acid materials include eicosapentaenoic acid or EPA (20:5 n-3), linoleic acid (18:2 n-6), γ-linolenic acidic GLA (18:3 n-6) acids, α-linolenic acid (18:3 n-3), dihomo-γ-linolenic or DHGLA (20:3n-6, α-linolenic (18:3n-3), stearidonic acid (18:4 n-3), and combinations thereof.

The ARA and DHA components can be provided in the form of free fatty acids or from any known or otherwise suitable source, natural or synthetic, which ultimately provides infants with the desired fatty acid materials. Such other sources include monoglycerides, diglycerides, and triglycerides containing one or more of the desired fatty acids esterified to the glyceride backbone, including simple glycerides in which all esterified positions contain the same fatty acid or mixed glycerides which contain different esterified fatty acids. Such other sources also include phospholipids as a diglyceride in which the third position on the glycerol backbone is bonded to a nitrogen containing compound such as choline, serine, ethanolamine, inositol, and so forth, via a phosphate ester. Triglycerides and phospholipids are often classified as long chain or medium chain, according to the fatty acids attached thereto. In human milk about 98% of the fatty acids are in triglycerides. A "source" of the desired fatty acids for use in the method of the present invention may therefore include any of these forms of glycerides from natural or other origins.

The nutritional formulas to which the methods of the present invention are directed may further comprise a lipid component in addition to the source of ARA and DHA described herein before, non-limiting examples of which include lipids derived from plants, typically providing fatty acids only to about 18 carbons in length, such as borage, black currant seed, corn, coconut, canola, soybean, safflower, high oleic safflower, sunflower, high oleic sunflower, olive, evening primrose, cottonseed, rice bran, grapeseed, flaxseed, garlic, peanuts, almonds, walnuts, wheat germ, and sesame.

Other suitable lipid materials for use in addition to the source of ARA and DHA described hereinbefore include dairy products such as eggs and butterfat; fish oils, such as cod, menhaden, sardine, tuna and many other fish; certain animal fats, lard, tallow and microbial oils such as fungal and algal oils, some descriptions of which are set forth in U.S. Pat. No. 5,374,657, U.S. Pat. No. 5,550,156, and U.S. Pat. No. 5,658,767, which descriptions are incorporated herein by reference.

Notably, fish oils are a good source of the DHA component of the present invention. Other suitable sources include algal oils such as those from dinoflagellates of the class Dinophyceae, notably *Crypthecodinium cohnii* are also sources of DHA (including DHASCO™), as taught in U.S. Pat. Nos. 5,397,591; 5,407,957; 5,492,938; and 5,711,983. The genus *Mortierella*, especially *M. alpina*, and *Pythium insidiosum* are also good sources of ARA for use herein, including ARASCO™ as taught by U.S. Pat. No. 5,658,767 and as taught by Yamada, et al. J. Dispersion Science and Technology, 10(4&5), pp 561-579 (1989), and Shinmen, et al. Appl. Microbiol. Biotechnol. 31:11-16 (1989).

Nutrients

The infant nutritional formulas for use in the methods of the present invention preferably comprise sufficient types and amounts of nutrients to help meet the targeted needs of the intended user. These formulas typically comprise lipid (in addition to the source of ARA and DHA described herein), protein, and carbohydrate, and preferably further comprise one or more of vitamins, minerals, or combinations thereof.

The method of the present invention preferably provides infants with up to 100%, including from about 50% to 100%, of their daily caloric intake, more preferably in combination with some human milk.

Many different sources and types of carbohydrates, lipids, proteins, minerals and vitamins are known and can be used in the infant formulas for use in the method of the present invention, provided that such nutrients are compatible with the added ingredients in the selected formulation, are safe and effective for their intended use, and do not otherwise unduly impair product performance.

The term "protein" as used herein, unless otherwise specified, includes intact and hydrolyzed proteins, free amino acids, and combinations thereof. Proteins suitable for use herein can therefore be hydrolyzed, partially hydrolyzed or non-hydrolyzed, and can be derived from any known or otherwise suitable source such as milk (e.g., casein, whey), animal (e.g., meat, fish), cereal (e.g., rice, corn), vegetable (e.g., soy), or combinations thereof. The protein can include, or be entirely or partially replaced by, free amino acids known or otherwise suitable for use in nutritional products, non-limiting examples of which include tryptophan, glutamine, tyrosine, methionine, cysteine, carnitine, arginine, and combinations thereof.

Non-limiting examples of lipids suitable for use in the nutrition formulas hereof, in addition to the sources of ARA and DHA described herein, include coconut oil, soy oil, corn oil, olive oil, safflower oil, high oleic safflower oil, MCT oil (medium chain triglycerides), sunflower oil, high oleic sunflower oil, structured triglycerides, palm and palm kernel oils, palm olein, canola oil, marine oils, cottonseed oils, and combinations thereof.

The infant nutrition formulas may further comprise any of a variety of vitamins, non-limiting examples of which include vitamin A, vitamin D, vitamin E, vitamin K, thiamine, riboflavin, pyridoxine, vitamin $B_{12}$, niacin, folic acid, pantothenic acid, biotin, vitamin C, choline, inositol, salts and derivatives thereof, and combinations thereof.

The infant nutrition formulas may further comprise any of a variety of minerals known or otherwise suitable for us in infant nutrition formulas, non-limiting examples of which include calcium, phosphorus, magnesium, iron, zinc, manganese, copper, iodine, sodium, potassium, chloride, selenium, and combinations thereof.

The infant nutrition formulas of the present invention preferably comprise nutrients in accordance with the relevant mint formula guidelines for the targeted consumer or user population, an example of which would be the infant Formula Act, 21 U.S.C. Section 350(a). Preferred carbohydrate, lipid, and protein concentrations for use in the formulas are set forth in the following table;

TABLE 2

Infant Formula Nutrients*

| Nutrient | Range | gm/100 kcal | gm/100 gm powder | gm/liter as fed |
|---|---|---|---|---|
| Carbohydrate | 1st embodiment | 8-16 | 30-90 | 54-108 |
| | 2nd embodiment | 9-13 | 45-60 | 61-88 |
| Lipid | 1st embodiment | 3-8 | 15-35 | 20-54 |
| | 2nd embodiment | 4-6.6 | 25-25 | 27-45 |
| Protein | 1st embodiment | 1-3.5 | 8-17 | 7-24 |
| | 2nd embodiment | 1.5-3.4 | 10-17 | 10-23 |

*all numerical values are preferably modified by the term "about"

The infant nutrition formula also includes those embodiments that comprise per 100 kcal of formula one or more of the following: vitamin A (from about 250 to about 750 IU), vitamin D (from about 40 to about 100 IU), vitamin K (greater than about 4 μm), vitamin E (at least about 0.3 IU), vitamin C (at least about 8 mg), thiamine (at least about 8 μg), vitamin $B_{12}$ (at least about 0.15 μg, niacin (at least about 250 μg), folic acid (at least about 4 μg), pantothenic acid (at least about 300 μg), biotin (at least about 1.5 μg), choline (at least about 7 mg), and inositol (at least about 2 mg).

The infant nutrition formula also includes those embodiments containing per 100 kcal of formula one or more of the following: calcium (at least about 50 mg), phosphorus (at least about 25 mg, magnesium (at least about 6 mg), iron (at least about 0.15 mg), iodine (at least about 5 μg, zinc (at least about 0.5 mg), copper (at least about 60 µg, manganese (at least about 5 µg, sodium (from about 20 to about 60 mg), potassium (from about 80 to about 200 mg, chloride (from about 55 to about 150 mg) and selenium (at least about 0.5 mcg).

Product Form

The nutritional formulas for use in the method of the present invention can be prepared in any of a variety of product forms, but will most typically be in the form of a ready-to-feed liquid, a liquid concentrate diluted prior to consumption, or a powder that is reconstituted prior to consumption.

The infant nutritional formulas for use in the method of the present invention can have or otherwise provide a variety of caloric densities depending upon the particular needs of the infant, but will most typically have or otherwise provide a caloric density of at least about 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter).

Preferred for preterm infants are the 22-24 kcal/fl oz formulas, including 22-23 kcal/fl oz formulas. For term its, preferred are the 20-21 kcal/fl oz (675-680 to 700 kcal/liter) formulas.

Method of Use

The method of the present invention comprises feeding to an infant, preterm or term, a nutritional formula having the requisite DHA and ARA components as described herein, to provide the infant with reduced body fat weight and increased lean body weight over time without impacting total overall growth. The feeding can be by any conventional or known method for feeding infants, preferably by oral administration, with the nutritional intake ranges preferably falling within the values described herein.

The method of the present invention provides up to 100% of the infants daily nutrition, typically from about 50% to 100%, but is preferably used in combination with human milk as well. The feeding method is continued for a period of time up to about 1 year corrected age for the infant, including up to about 3 months, including up to about 6 months, including up to about 9 months, corrected or conventional age of the infant.

The method of the present invention may be applied to both term and preterm infants, but is preferably applied to preterm infants as defined herein.

In the context of the method of the present invention as applied to infant nutritional formulas in powder form, the corresponding method may further comprise reconstituting the powder with an aqueous vehicle, most typically water or human milk to form the desired caloric density, which is then orally or enterally fed to the infant to provide the desired nutrition. For powdered infant formula embodiments of the present invention, each is reconstituted with a quantity of water or other suitable fluid such as human milk to produce a volume suitable for one infant feeding, but generally from about 8 grams to about 9 grams of powder are reconstituted with about 55 to about 65 ml of water to produce the desired nutrient densities.

Optional Ingredients

The infant formulas for use in the method of the present invention may further comprise other optional components that may modify the physical, chemical, aesthetic or processing characteristics of the formulas or serve as pharmaceutical or additional nutritional components when used in the targeted population. Many such optional ingredients are known for use in food and nutritional products, including infant formulas, and may also be used in the infant formulas for use in the method of the present invention, provided that such optional materials are compatible with the essential materials described herein, are safe and effective for their intended use, and do not otherwise unduly impair product performance.

Non-limiting examples of such optional ingredients include preservatives, additional anti-oxidants, emulsifying agents, buffers, colorants, flavors, nucleotides and nucleosides, thickening agents, fiber, stabilizers, and so forth.

Method of Manufacture

The infant formulas of the present invention may be prepared by any known or otherwise effective technique, suitable for making and formulating infant or similar other formulas. Many such methods are described in the relevant arts or are otherwise well known to those skilled in the nutrition formula art.

The nutritional formulas for use in the method of the present invention can be prepared by any of a variety of known or otherwise effective methods. These methods typically involve the initial formation of an aqueous slurry containing carbohydrates, proteins, lipids, stabilizers or other formulation aids, vitamins, minerals, or combinations thereof. The slurry is emulsified, homogenized and cooled. Various other solutions, mixtures or other materials may be added to the resulting emulsion before, during, or after further processing. This emulsion can then be further diluted, sterilized, and packaged to form a ready-to-feed or concentrated liquid, or it can be sterilized and subsequently processed and packaged as a reconstitutable powder (e.g., spray dried, dry mixed, agglomerated).

Other methods for making infant nutrition formulas are described, for example, in U.S. Pat. No. 6,365,218 (Borschel), which description is incorporated herein by reference.

The infant nutritional formulas for use in the method of the present invention can also be obtained from commercially available formulas, provided that such formulas contain the requisite DHA and ARA components. Non-limiting examples of such commercially available formulas for use in the method hereof include Similac® Advance® Infant Formula (milk protein based 20 Cal/fl oz), Isomil® Advance® Infant formula (soy protein-based 20 Cal/fl oz), Similac® Special Care® Advance Premature Infant Formula (20 and 24 kcal/fl oz), Similac® NeoSure® Advance® Nutrient-enriched Post-discharge Formula (744 Cal/L), all of which are available from Ross Products Division, Abbott Laboratories, Columbus, Ohio, USA. Other non-limiting examples of suitable formulas for use in the method of the present invention include those Enfamil® brand Infant formulas containing both DHA and ARA under the LIPIL® trademark, which formulas are available from Mead Johnson & Company, Evansville, Ind., USA.

Example

The following clinical study was performed in accordance with the method of the present invention. As shown from the experimental data set forth hereinafter, the method resulted in increased lean body mass and reduced fat body mass in the subject infants, without an impact on overall growth.

1.1. Clinical Study: Summary

The objective of the study was to evaluate body composition of premature infants fed formulas with arachidonic acid (ARA; 20:4n6), and docosahexaenoic acid (DHA; 22:6n3) to one year of gestation-corrected age (CA). Preterm infants (750-1800 g birth weight and <33 wks gestational age) were assigned within 72 hrs of their first enteral feeding to 1 of 3 formulas: control (n=22); DHA+ARA from fish/fungal oil (DHA+ARA[FF], n=20); or DHA+ARA from egg/fish oil (DHA+ARA[EF], n=18). Infants were fed human milk and/or preterm formulas with or without 0.26% DHA and 0.42% ARA to term corrected age (CA) followed by human milk or post-discharge preterm formulas with or without 0.16% DHA and 0.42% ARA to 12 m CA. Body composition was measured by dual-energy x-ray absorptiometry (DEXA).

The DHA+ARA supplemented infants did not differ in longitudinal growth compared with control infants from 40 wks to 12 m CA. Bone mineral content and bone mineral density similarly did not differ among groups. At 12-months CA, infants fed DHA+ARA supplemented formulas had significantly greater lean body mass (p<0.03) and significantly less fat mass (p<0.02) than infants fed the unsupplemented control formula The DHA+ARA supplemented formulas, therefore, had no effect on growth or bone mineralization in premature infants <33 wks gestation. Preterm formulas with BHA+ARA at the levels and ratios in this study and fed up to one year CA led to increased lean body mass and reduced fat mass by one-year of age.

1.2. Clinical Study Background

The long-chain polyunsaturated fatty acids docosahexaenoic acid (DHA) and arachidonic acid (ARA) are currently added to infant formulas in many countries. ARA and DHA are the predominant long-chain polyunsaturated fatty acids in the central nervous system, and it has been postulated that an adequate dietary supply during infancy is necessary to support optimum neurodevelopment. The results of numerous investigations indicate that visual acuity and neurocognitive development are enhanced in preterm infants fed formulas supplemented with DHA or both ARA and DHA reviewed in (1-4). Most (3, 5-7) but not all (8) studies have reported normal growth in preterm infants fed formulas supplemented with both ARA and DHA.

Long chain polyunsaturated fatty acids, including ARA, DHA and EPA, are important biomediators that can impact growth and body composition through diverse mechanisms. The level and ratio of long-chain polyunsaturated fatty acids fed can influence cell membrane properties, cell-to-cell signaling processes, the expression of genes that regulate cell differentiation- and growth, and the synthesis of eicosanoids that affect bone metabolism (9). Animal studies suggest that dietary long-chain polyunsaturated fatty acids can affect both fat mass and distribution (10, 11) and bone metabolism (12, 13).

There is little information available regarding the effects of dietary long-chain polyunsaturated fatty acids on body composition in neonatal (infant) animals or in humans. In the present study, growth and body composition were investigated in preterm infants fed formulas supplemented with ARA and DHA from first enteral formula feedings to one-year term corrected age.

1.3. Study Design

This controlled, double-blind, randomized, parallel study was designed to evaluate body composition in premature infants fed one of two formulas with different sources of DHA and ARA (DHA+ARA) or a control formula with no added DHA or ARA to 12 months gestation-corrected age (CA). Assessments were made at the time enteral feedings were begun (Study Day 1), at 35 weeks CA, 40 weeks CA (term), 4 months CA and 12 months CA. Study feedings were 24 kcal/fl oz preterm infant formulas from Study Day 1 to 40 weeks CA, and 22 kcal/fl oz post-discharge formulas from 40 weeks CA to 12 months CA.

1.4. Subjects

Sixty preterm infants with birth weights from 750 to 1800 g and gestational age <33 weeks were recruited and evaluated in the study. These infants were enrolled within 72 hours of their first enteral feeding, and could be enrolled as long as the enteral feeding was initiated by the twenty-eighth day of life. Infants with one or more of the following conditions prior to randomization were excluded: congenital abnormalities that could affect growth or development, major surgery, Grade III or IV periventricular hemorrhage, asphyxia resulting in severe and permanent neurological damage, treatment with extracorporeal membrane oxygenation, maternal incapacity (including sub stance abuse), or uncontrolled systemic infection. There were no restrictions on the type of feeding prior to study entry.

The randomization schedule was stratified by gender and birth weight groups (750 to 1250 gm and 1251 to 1800 gm). If twins were enrolled, both twins were assigned to the same formula group using a separate randomization schedule prepared for twin births.

1.5 Study Feedings

Study feedings were those described herein (3). Briefly, preterm infants were fed 24 kcal/fl oz Similac® Special Care® containing DHA (0.26%) and ARA (0.42%) either from fungal oil and fish oil (DHA+ARA [FF]), or from egg-derived triglyceride and fish oil (DHA+ARA [EF]) from the first enteral formula feeding until 40 weeks CA. Infants in the control group (control) were fed 24 kcal/fl oz Similac® Special Care®. At 40 weeks CA, infants were switched to 22 kcal/fl oz NeoSure® (control), or to NeoSure® with DHA (0.16%) and ARA (0.42%) from the same sources that were fed previously. The fatty acid composition of the formulas is described hereinafter in Table 3.

Human milk feeding was encouraged prior to initiating formula feeding and throughout the entire study for infants in each group. Human milk was provided as expressed milk fed by tube or bottle, or by nursing at the breast. If the amount of milk produced by the mother was insufficient to meet the volume and energy needs of the infant, the randomly assigned study formula was to be fed. During hospital stay, it was recommended that expressed human milk be fortified to achieve an energy density of 22 to 24 kcal/fl oz. Infants were categorized as exclusively formula-fed or as receiving mixed formula-human milk feedings. Exclusive formula feeding was defined as less than a total of 100 ml/kg birth weight of in-hospital human milk intake (approximately 130 ml) and formula for more than 80% of feedings from hospital discharge to term CA. All other infants were placed in the "formula plus human milk" group. The fatty acid composition of the study formulas is shown on Table 1.

1.6 Feeding Procedures

Study Day 1 was the day the infant was randomized and began enteral feeding of the assigned study formula or human milk. In-hospital, parenteral nutrition was administered to infants who could not tolerate full enteral feeding. A daily record was kept of the volume of parenteral nutrition, study formula and human milk provided. The use of supplemental multi-vitamins and/or minerals was permitted as indicated by the attending physician. Enteral feedings were withheld at the discretion of the attending physician if the infant showed signs of intolerance to the formula, and were reintroduced after indicators of intolerance resolved. If radiographic evidence of necrotizing enterocolitis (NEC) occurred, or if NEC was documented at surgery, the subject was removed from the study.

Infants were fed the 24 kcal/fl oz study feedings from Study Day 1 to 40 weeks CA and 22 kcal/fl oz study feedings from 40 weeks CA to 12 months CA. For three consecutive days prior to the 40-week CA, 4-month CA and 12-month CA assessments, parents were asked to keep diaries to record formula intake, frequency of breastfeeding, use of multivitamin and mineral supplements, and other foods consumed. Parents were encouraged to delay the introduction of solid foods until infants were at least 2 months CA.

1.7 Anthropometric Data

Birth weight, length and head circumference measurements were obtained from the medical record. In-hospital, weights were measured daily, and length and head circumference were measured weekly. Post-discharge weight, length and head circumference were recorded at 35 and 40 weeks CA, and at 4 and 12 months CA. Approximately 25% of the 35-week CA visits, 94% of the 40-week CA visits, and 100% of the 4 and 12 month CA visits were post-discharge. At each assessment, weight measurements were obtained once (in-hospital) or twice (post-discharge). Recumbent length and head circumferences were obtained twice. If the two measurements were not within specified tolerances (weight ±10 g, and length and head circumference ±0.5 cm), a third measurement was taken. Multiple measurements were averaged for statistical analyses.

Infants were weighed nude in-hospital and after hospital discharge using calibrated digital electronic scales (Olympia Smart Scales, Olympia Medical Systems, Seattle, Wash., and Scale Tronix, Wheaton Ill., respectively). Lengths were measured using a standard length board sized for either preterm or term infants (Ellard Instrumentation Ltd., Seattle, Wash.). Head circumferences were measured using the Ross Laboratories INSER-TAPE®.

Dual Energy X-Ray Absorptiometry (DEXA)

DEXA measurements were made with a whole body scanner (Hologic QDR 2000/W Densitometer, Infant Whole Body Software Version 5.71P; Hologic, Inc., Bedford, Mass.) operated in the single beam mode. All DEXA technicians had completed certification to operate the densitometer. One technician made over 75% of the DEXA measurements. Quality control scans using the manufacturer-supplied step-phantom were performed according to hospital protocol. Measurements of total body bone mineral content (g), total body bone mineral density (g/cm$^2$), total body fat (kg) and total lean mass (kg) were made at 35 and 40 weeks CA, and at 4 and 12 months CA. Infants wore only disposable diapers, were swaddled in a blanket or sheet, and were placed on a blanket on top of the pediatric platform and next to the step-phantom block, both supplied by the manufacturer. Infants were near sleep or fully asleep before scanning was started. No sedation was used. Scanning was continued until a complete scan was obtained that included no more than three visible partial breaks or not more than one complete break on the image, or until it became clear that the infant was unable to lay still for a sufficient period of time. One hour was used as the approximate maximum time to attempt completion of one usable scan. The average radiation dose of one infant whole body scan is estimated at 3 μSv (0.3 mrem). Bone mineral content (g) was sensitive to 0.01, bone mineral density (g/cm$^2$) to 0.001, and body fat and lean mass to 0.1 gram.

Blood Fatty Acid Analyses

Blood was collected by venipuncture at the 4 and 12 month CA visits for determination of the fatty acid composition of plasma and of the phosphatidylcholine (PC) and phosphatidylethanolamine (PE) membrane fractions of erythrocytes. Blood samples were processed and frozen at −70° C., and shipped on dry ice to a central laboratory (Analytical Research and Services, Ross Products Division, Columbus, Ohio) for analysis (14).

1.8 Statistical Analyses

The estimated sample size was targeted to detect a 0.5 standard deviation difference in fat free mass with 80% power using a 2-sided 0.05 level test. Preterm infants who were fed formulas with and without supplemental DHA and who had their fat free mass measured at 4 months CA were used to estimate variability (15).

Formula assignment was determined using a computer-generated randomization schedule based on a permuted blocks algorithm. Categorical demographic variables were evaluated using chi-square tests of association and Fisher's exact tests, while continuous demographic variables were evaluated using analysis of (co)variance (AN(C)OVA). Summary statics and distributional characteristics were obtained for all variables prior to analysis to identify outliers. Model fit was assessed using residual and stem-leaf plots for all parametric analyses of continuous variables.

Anthropometric and body composition data were assessed longitudinally using repeated measures analyses. The analysis of anthropometric measures included study feeding group, visit, gender, birth weight, mixed versus exclusive formula-feeding, and interactions between study feeding group and visit as terms in the model. The analysis of body composition measures included study feeding group, visit, gender, race, body weight at scan, mixed versus exclusive formula-feeding, and interactions between study feeding group and visit as terms in the model. Where the tests of interaction between feeding group and visit were significant, pair wise comparisons among the three feeding groups were performed for that visit.

Changes in bone mineral content between study visits were assessed for the following five intervals: 35 weeks to 40 weeks CA, 4 months, 12 months CA, and 40 weeks to 4 months and 12 months CA. The ANCOVA model for bone mineral content data included terms for study feeding group, gender, mixed versus exclusive formula-feeding, race, and average body weight between DEXA measurements.

All hypothesis testing was 2-sided at the 5% level for main effects and at the 15% level for interaction tests. Post-hoc pair wise comparisons following significant interaction tests were done using t-tests for differences between least-squares means (group means adjusted for the other terms in the analysis model). No adjustments were made for multiplicity of endpoints tested in this study. All analyses were done using PC SAS® version 8.2 (PROC ED, PROC GLM, PROC FREQ and PROC UNIVARIATE).

1.9 Results

Sixty infants were randomized. One infant diagnosed with a rare neurological disorder, and two infants who were exclusively human milk-fed throughout the study were excluded from the analyses. Birth anthropometrics, gestational age, gender, ethnicity, percent of infants with birth weight appropriate for gestational age, percent of infants in each birth weight group, 5 minute Apgar scores, postnatal complication rate and amount of human milk intake did not differ among study groups (Table 4). There were significantly more twin births in the DHA+ARA [F] group compared with the DHA+ARA [FF] and control groups. The numbers of analyzable subjects at the Study Day 1, 35 week, 40 week CA, 4 month CA and 12 month CA visits were 57, 55, 53, 45 and 41, respectively. Sixteen subjects dropped out of the study between Study Day 1 and the 12-month CA visit The reasons for early exit included switching to a non-study formula per physician recommendation (Control, n=7; DHA+ARA [FF], n=0; DHA+ARA [EF], n=1), voluntary withdrawal by parent or investigator (Control, n=0; DHA+ARA [FF], n=0; DHA+ARA [EF], n=2), non-compliance with study visits (Control, n=0; DHA+ARA [FF], n=3; DHA+ARA [EF], n=2), and death unrelated to study participation (Control, n=0; DHA+ARA [FF], n=1; DHA+ARA [EF], n=0).

Postnatal ages at each study time point were not significantly different among the three groups (data not shown). Enteral energy intakes were not significantly different among the three groups. From Study Day 1 to hospital discharge, and at 40 weeks, 4 months and 12 months CA, enteral energy intakes (kcal/kg per day) for the DHA+ARA [FF], DHA+ARA [EF], and control groups were, respectively, 93±11, 99±9, 95±3 (p=0.910), 120±8, 120±17, 116±6 (p=0.968), 100±7, 107±19, 114±12 (p=0.764) and 71±11, 88±14, 67±7 (p=0354).

No differences in the percent of infants with a patent ductus arteriosus, bronchopulmonary dysplasia, or a grade III/IV IVH were found; 22.2%, 22.2% and 33.3% for infants in the DHA+ARA [FF], DHA+ARA [EF] and control groups, respectively (p=0.656). No infants developed confirmed NEC.

Plasma levels of ARA and DHA were significantly lower in the control versus the experimental groups. At 4 months CA, plasma levels of ARA (wt %) for the DHA+ARA [FF], DHA+ARA [EF], and control groups were, respectively, 12.0±0.5, 12.0±0.6, and 8.6±0.9 (p<0.01); and at 12 months CA were 13.2±1.1, 12.5±0.6, and 9.6±0.8 (p<0.01). At 4 months CA, plasma levels of DHA (wt %) for the DHA+ARA[FF], DHA+ARA [EF], and control groups were, respectively, 3.4±0.1, 3.2±0.2, and 1.8±0.2 (p<0.001); and at 12 months CA were 3.8±0.3, 3.5±0.2, and 1.8±0.2 (p<0.001). At 12 months CA, erythrocyte PE and PC DHA levels were significantly lower in the control versus the experimental groups (p<0.04). Throughout the study, there were no significant differences in erythrocyte PE and PC ARA levels among the three study groups (data not shown).

There were no significant differences among the three study groups in the longitudinal analyses of weight, length, or head circumference (Table 5). There were no significant differences among the three study groups in bone mineral density or bone mineral content (Table 6). There were no significant differences among the groups for rate of bone mineral content gain between any interval measured. For example, increase in bone mineral content (g/d) for the DHA+ARA [FF], DHA+ARA [EF], and control groups from 35 to 40 weeks was 0.54±0.05, 0.52±0.05, and 0.58±0.05, respectively, from 40 weeks to 4 months corrected age was 0.63±0.03, 0.70±0.05, and 0.66±0.04, respectively, and from 40 weeks to 12 months corrected age was 0.38±0.03, 0.40±0.04, and 0.43±0.03, respectively. Similarly, there were no significant differences in the rate of bone mineral content gain from 35 weeks to 4 months CA, or between 35 weeks and 12 months CA (data not shown).

Figure 1A:
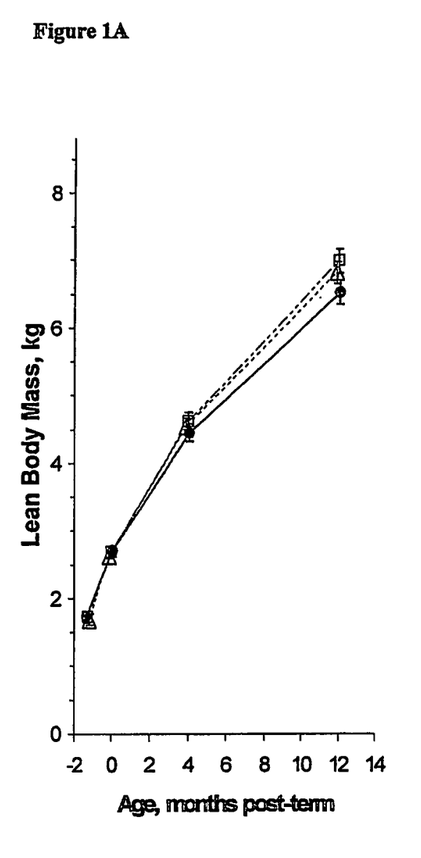
FIGS. 1A and 1B illustrate some of the clinical data described hereinafter, including lean body mass (FIG. 1A) and fat mass (FIG. 1B) at 35 and 40 weeks CA (corrected age), and at 4 and 12 months CA, in preterm infants fed formulas containing a combination of DHA and ARA or an unsupplemented control formula. Data points represent least squares means adjusted for gender, race, body weight and human milk intake. At 12 months, lean body mass was significantly greater ($p \leq 0.03$), and fat mass significantly less ($p \leq 0.01$) in infants fed formulas supplemented with DHA and ARA with either the fish-fungal (DHA+ARA[FF]; open triangles) or egg-fish (DHA+ARA[EF]; open squares) oils compared with infants fed control formulas (closed circles).
Figure 1B:
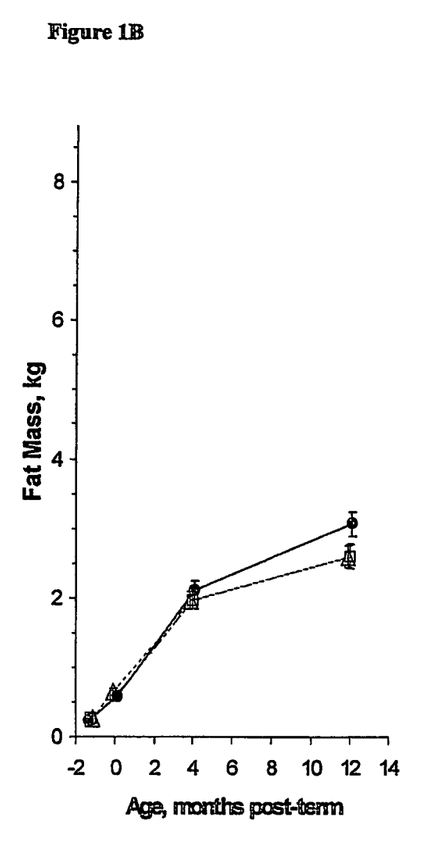

At the 12 month CA visit, there were significant feeding group-by-visit interactions for both fat mass (p<0.03) and lean body mass (p=0.13). Infants fed formula supplemented with DHA and ARA from either the fish-fungal oil [FF]; or the egg-fish oil [EF] had significantly greater lean body mass (p<0.03, p<0.01, respectively), and significantly less fat mass (p<0.01, p<0.02, respectively) compared with infants fed the control formula (Table 6). The least squares adjusted means (±SEM) at 12 months CA for lean body mass (kg) for infants in the control, DHA+ARA [FF] and DHA+ARA [EF] groups were 6.53±0.15, 6.83±0.13, and 7.00±0.14, respectively, and for fat mass (kg) were 3.07±0.14, 2.60±0.12, and 2.60±0.13, respectively, (FIG. 1).

1.10 Discussion

Very low birth weight infants are commonly discharged from the hospital on nutrient enriched feedings. Twenty-two kcal/oz formulas, such as those used in the present study, are increasingly prescribed. Several studies reported that post-discharge nutrient enriched feedings are associated with significant improvements in catch-up growth (16-19) and may be particularly advantageous for males and for infants with the lowest birth weights (16, 17). Short-term feeding of preterm formulas is not associated with changes in plasma mineral concentration (20) but feeding of nutrient enriched formulas appears to result in increased bone mineralization (21-23). Short-term feeding of post-discharge formula to 2 months is not associated with changes in fat and lean body mass (24). This is the first study to report effects of DHA and ARA in formula on body composition in preterm infants. While there were no effects on bone mineral deposition, infants fed the DHA+ARA supplemented formulas from first enteral feedings to 12 months CA had greater lean body mass and reduced fat mass at 12 months.

Preterm infants fed formula during the early postnatal period accumulate fat faster than fetuses of similar postconceptional age (25). It has been suggested that dietary practices after hospital discharge have an even greater impact on body composition than dietary practices in-hospital (26). However, there is a paucity of data regarding the effect of the post-discharge diet on body composition in preterm infants. Ryan et al. (15) reported lower fat free mass in preterm male infants who were fed preterm formula supplemented with 0.2% DHA but no ARA until 43 weeks postmenstrual age followed by term formula similarly supplemented with DHA until 45 months corrected age. By contrast, preterm infants in the present study fed formulas with both DHA+ARA, regardless of source, to 12 months CA had more lean body mass (average LS mean difference, 300-470 g), less fat mass (average LS mean difference, 470 g), and no differences in overall weight than the control group. The longitudinal values for fat mass in the present study are in agreement with those recently reported for a group of 104 healthy, term or near term infants who were either breast fed or fed term infant formula (27).

When considering animal (11, 28-34) and infant (15) studies examining body composition, the increase in lean body mass and corresponding reduced fat mass in the preterm infants in the present study were not anticipated. In studies with rodents, diets rich in the long-chain n-3 fatty acids, DHA and EPA, from fish oil have been associated with lower body fat when compared with diets rich in saturated fat (e.g., lard, MCT oil) or polyunsaturated fatty acids such as linoleic acid (e.g. corn oil) (11, 28-34). Adult rats fed the diets rich in DHA and EPA had preferential partitioning of ingested energy toward oxidation at the expense of storage (28), reduced fat mass (29), decreased fat cell trophic growth (30), altered expression of genes involved in adipose tissue metabolism (11) including lipoprotein lipase activity (32), increased peroxisomal beta-oxidation (33), reduced adipocyte cell volumes (34), increased visceral fat hypertrophy (10), and altered regulation of leptin (35). These studies, however, did not examine diets rich in ARA to evaluate possible interactions between high dietary DHA and EPA and dietary ARA. Additionally, more than 25 and 150 fold greater amounts of DHA and EPA, respectively, were fed in the rodent studies than in the present and other (15) infant formula studies that have examined body composition. In the study by Ryan et al (15), preterm infants were fed formulas with DHA and EPA at less than 0.3% of calories for about five months after hospital discharge. Infants fed the supplemented formulas grew slower and had lower fat-free mass, but fat mass was not different than in infants fed the unsupplemented control formula. Conversely, growth is not slower in preterm infants fed formulas containing both ARA and DHA compared with an unsupplemented control formula (7, 36-38), and as shown in the present study lean body mass is greater and fat mass is reduced. Additional studies are needed to understand the specific effects of ARA and the long chain n-3 fatty acids, DHA and EPA, on lean body mass and fat mass in infancy.

In the present study, preterm infants fed preterm formulas supplemented with DHA and ARA for the first year of life accumulated fat and lean body mass differently than preterm infants fed unsupplemented preterm formulas for the first year of life. In term-born infants, birth weight appears to be directly correlated with fat-free mass later in life (8). When compared to appropriately grown newborns, the reduced weight of small-for-gestational age (SGA) infants at birth is primarily due to lower lean body mass with adiposity less affected (39). An overall deficit in muscularity and a tendency for a higher percent body fatness persists through the first years of life in infants born SGA (40). Intrauterine growth restriction and SGA status at term have been linked to increased risk of adult disease (41-43). Independent of size at birth, both slow and accelerated weight gain during infancy is associated with an increased risk of adult disease (44).

Preterm infants often experience postnatal growth restriction and have anthropometric measurements at less than the 10$^{th}$ percentile at the time of hospital discharge (45, 46). They are also at risk for poor growth into childhood (47). Little is known how postnatal growth patterns influence the body composition of VLBW, preterm infants. The present study suggests that feeding low birthweight infants during the first year of life with preterm formulas supplemented with DHA and ARA results in a body composition in which total fat mass is reduced and lean body mass enhanced.

In the present study, neither bone mineral content nor bone mineral density were different between 35 weeks and 12 months CA in preterm infants fed either unsupplemented preterm formulas or preterm formulas supplemented with DHA and ARA for the first year of life. Consistent with these findings, Martinez et al. (6) reported that supplementation of preterm formula with ARA and DHA caused no disturbances in mineral balance. Studies with rodents (13, 48, 49), piglets (50, 51), and chicks (52, 53), on the other hand, have reported effects of no fatty acids (i.e. linoleic acid; ARA) and n-3 fatty acids (i.e. EPA; DHA) on bone formation. ARA (net) and EPA (n-3) are precursors to eicosanoids that influence the differentiation and activation of cells in bone and cartilage tissue. For example, in a study with formula-fed piglets, ARA and prostaglandin E2 ($PGE_2$), synthesized from ARA, both increased bone mass, apparently by independent, distinct mechanisms (50). Others report concentration dependent effects of $PGE_2$ with higher levels associated with depressed bone formation (13, 52). Another study with formula-fed piglets reported that higher plasma DHA was associated with less bone resorption (53). Watkins et al (54), on the other hand, reported that chicks fed diets rich in n-6 fatty acids led to increased levels of PGE2 and depressed bone formation rates compared with animals fed diets high in n-3 fatty acids. It is not known whether different levels or ratios of ARA, EPA and DHA than those fed in the present study may affect bone formation in preterm infants. Further studies are warranted given the rapid bone remodeling that occurs during the first year of life in preterm infants (55). The results of the present study suggest that DHA and ARA supplemented infant formulas can be fed to preterm infants for their neurodevelopment and visual acuity advantages without negative affects on bone mineralization.

The growth results of the present study are in agreement with those of the larger study of O'Connor et al. (3) with 470 preterm infants given the identical formulas used in the present study and fed for the same period of time. O'Connor et al. found no consistent differences among the groups in weight, length, or head circumference. In several early studies, growth was restricted in preterm infants fed formulas supplemented with only n-3 fatty acids, as DHA alone or in combination with EPA, and no ARA (n-6 fatty acids) (15, 56, 57). In most studies in which preterm and term infants were fed formulas supplemented with both n-6 (ARA) and n-3 (DHA) fatty acids, and little or no EPA, no adverse effects on growth were reported (7, 36-38). Innis et al. (5) reported that infants fed preterm formula supplemented with DHA and ARA gained weight significantly faster than infants fed a standard unsupplemented preterm formula. Longitudinal growth was affected in one study designed to evaluate the neurodevelopmental outcome of preterm infants fed preterm formulas with and without DHA and ARA (8). The infants fed DHA and ARA supplemented preterm formula were 1.5 cm shorter at 18 months CA than infants fed an unsupplemented control preterm formula (8). The supplemented formula was fed for 3-4 weeks, compared to 12-14 months in the present study, and contained lower concentrations and different ratios of DHA and ARA than the study products used in the present study. Taken together, the growth data from this study and from previous reports suggest that preterm and discharge formulas supplemented with DHA and ARA support adequate growth of preterm infants.

1.11 Tables

TABLE 3

Fatty acid composition of study formulas. Values are mean (g/100 g) of total fatty acids.

| Fatty Acid | 24 kcal/fl oz formula | | | 22 kcal/fl oz formula | | |
|---|---|---|---|---|---|---|
| | DHA + ARA [FF] | DHA + ARA [EF} | Control | DHA + ARA [FF] | DHA + ARA [EF] | Control |
| 6:0 | 0.34 | 0.32 | 0.38 | 0.27 | 0.22 | 0.24 |
| 8:0 | 29.8 | 29.6 | 30.4 | 17.0 | 15.8 | 16.1 |
| 10:0 | 21.2 | 20.9 | 21.3 | 10.6 | 10.6 | 11.2 |
| 12:0 | 8.1 | 5.8 | 9.4 | 8.5 | 6.1 | 9.5 |
| 14:0 | 3.2 | 2.3 | 3.6 | 3.4 | 2.4 | 3.7 |

TABLE 3-continued

Fatty acid composition of study formulas. Values are mean (g/100 g) of total fatty acids.

|  | 24 kcal/fl oz formula | | | 22 kcal/fl oz formula | | |
|---|---|---|---|---|---|---|
| Fatty Acid | DHA + ARA [FF] | DHA + ARA [EF] | Control | DHA + ARA [FF] | DHA + ARA [EF] | Control |
| 16:0 | 5.5 | 6.4 | 5.3 | 6.4 | 7.4 | 6.3 |
| 18:0 | 2.7 | 3.4 | 2.6 | 2.4 | 3.2 | 2.4 |
| 18:1 | 8.4 | 9.8 | 8.2 | 27.9 | 29.8 | 28.3 |
| 18:2n6 | 16.8 | 17.5 | 16.0 | 19.5 | 20.3 | 19.1 |
| 18:3n3 | 2.6 | 2.5 | 2.4 | 2.4 | 2.4 | 2.4 |
| 20:4n6 (ARA) | 0.43 | 0.41 | ND | 0.43 | 0.41 | ND |
| 20:5n3 (EPA) | 0.08 | ND | ND | ND | ND | ND |
| 22:6n3 (DHA) | 0.27 | 0.24 | ND | 0.16 | 0.15 | ND |

ND indicates below the detection limit of the analyses

TABLE 4

Characteristics of preterm infants fed formulas with DHA and ARA or unsupplemented control formulas.

|  | DHA + ARA [FF] | DHA + ARA [EF] | Control | p-values |
|---|---|---|---|---|
| Sample size, n | 18 | 18 | 21 |  |
| Birth weight, g | 1424 ± 78 | 1363 ± 57 | 1322 ± 59 | 0.495 |
| Birth length, cm | 39.1 ± 0.8 | 39.6 ± 0.6 | 38.3 ± 0.6 | 0.373 |
| Birth head circumference, cm | 27.9 ± 0.5 | 27.3 ± 0.5 | 27.4 ± 0.4 | 0.681 |
| Gestational age, weeks | 30.6 ± 0.6 | 30.4 ± 0.5 | 30.0 ± 0.5 | 0.695 |
| Postnatal age at study day 1 | 5.7 ± 0.9 | 3.7 ± 0.9 | 5.5 ± 0.9 | 0.190 |
| Ethnicity % (n) |  |  |  |  |
| White | 56 (10) | 28 (5) | 33 (7) | 0.190 |
| Non-white | 44 (8) | 72 (13) | 67 (14) |  |
| Gender, % (n) |  |  |  |  |
| Males | 44 (8) | 56 (10) | 62 (13) | 0.547 |
| Multiple birth status, % (n) |  |  |  |  |
| Singleton | 72 (13)[a] | 44 (8)[b] | 81 (17)[a] | 0.046† |
| Twin | 28 (5) | 56 (10) | 19 (4) |  |
| Size at birth, % (n) |  |  |  |  |
| AGA | 100 (18) | 78 (14) | 91 (19) | 0.093 |
| SGA | 0 | 22 (4) | 9 (2) |  |
| Birthweight category, % (n) |  |  |  |  |
| ≤1250 g | 28 (5) | 28 (5) | 48 (10) | 0.318 |
| Apgar at 5 minutes, % (n) |  |  |  |  |
| ≥ 7 | 100 (17) | 89 (16) | 76 (16) | 0.086 |
| Feeding category, % (n) |  |  |  |  |
| Exclusive formula | 50 (9) | 72 (13) | 67 (14) | 0.352 |
| Formula plus human milk | 50 (9) | 28 (5) | 33 (7) |  |

Data are the mean ± SEM (number of subjects) unless otherwise indicated.
*ANOVA or chi-square.
†Different letters in the same row indicate significant pair wise differences among groups

TABLE 5

Weight, length, and head circumference of preterm infants fed formulas with DHA and ARA or unsupplemented control formulas.

|  | DHA + ARA [FF] | DHA + ARA [EF] | Control |
|---|---|---|---|
| WEIGHT (gm) |  |  |  |
| Study day 1 | 1349 ± 76 (18) | 1259 ± 57 (18) | 1230 ± 63 (21) |
| 35 weeks CA | 1871 ± 118 (17) | 1874 ± 85 (18) | 1916 ± 73 (18) |

TABLE 5-continued

Weight, length, and head circumference of preterm infants fed formulas with DHA and ARA or unsupplemented control formulas.

|  | DHA + ARA [FF] | DHA + ARA [EF] | Control |
|---|---|---|---|
| 40 weeks CA | 3147 ± 149 (18) | 3136 ± 105 (17) | 3280 ± 135 (18) |
| 4 months CA | 6154 ± 212 (16) | 6432 ± 217 (14) | 6524 ± 220 (14) |
| 12 months CA | 8977 ± 293 (14) | 9505 ± 243 (13) | 9343 ± 307 (14) |
| LENGTH (cm) | | | |
| Study day 1 | 39.0 ± 1.3 (7) | 40.9 ± 0.7 (8) | 38.2 ± 0.8 (8) |
| 35 weeks CA | 42.7 ± 0.7 (17) | 42.7 ± 0.5 (18) | 42.5 ± 0.5 (18) |
| 40 weeks CA | 48.2 ± 0.7 (18) | 48.1 ± 0.5 (17) | 48.0 ± 0.7 (18) |
| 4 months CA | 60.9 ± 0.6 (16) | 62.8 ± 0.7 (14) | 61.8 ± 0.7 (14) |
| 12 months CA | 75.2 ± 0.9 (14) | 76.3 ± 0.8 (13) | 73.9 ± 0.9 (14) |
| HEAD CIRCUMFERENCE (cm) | | | |
| Study day 1 | 27.0 ± 0.9 (7) | 28.4 ± 0.4 (9) | 26.4 ± 0.6 (8) |
| 35 weeks CA | 30.6 ± 0.5 (17) | 30.3 ± 0.4 (18) | 30.8 ± 0.2 (18) |
| 40 weeks CA | 34.5 ± 0.5 (18) | 35.0 ± 0.3 (17) | 35.4 ± 0.3 (18) |
| 4 months CA | 41.1 ± 0.6 (16) | 42.0 ± 0.3 (14) | 41.9 ± 0.4 (14) |
| 12 months CA | 46.0 ± 0.4 (14) | 46.2 ± 0.4 (13) | 46.2 ± 0.4 (14) |

Data are reported as the unadjusted mean ± SEM (number of subjects)

*Differences among groups were determined using repeated measures ANCOVA controlling for visit, gender, human milk intake, birth weight, and feeding group-by-visit interactions. No significant feeding group differences (p > 0.05) were found.

TABLE 6

Body composition measurements in preterm infants fed formulas with DHA and ARA or unsupplemented control formulas at 35 weeks, 40 weeks CA, and 4 and 12 months CA.

|  | DHA + ARA [FF] | DHA + ARA [EF] | Control |
|---|---|---|---|
| BONE MINERAL DENSITY (g/cm$^2$) | | | |
| 35 weeks CA | 0.145 ± 0.004 (17) | 0.146 ± 0.004 (18) | 0.140 ± 0.004 (18) |
| 40 weeks CA | 0.170 ± 0.005 (18) | 0.165 ± 0.004 (17) | 0.172 ± 0.005 (17) |
| 4 months CA | 0.257 ± 0.006 (15) | 0.258 ± 0.007 (12) | 0.263 ± 0.008 (12) |
| 12 months CA | 0.323 ± 0.010 (12) | 0.324 ± 0.008 (11) | 0.333 ± 0.009 (10) |
| BONE MINERAL CONTENT (g) | | | |
| 35 weeks CA | 28.8 ± 1.9 (17) | 28.1 ± 1.6 (18) | 26.8 ± 1.5 (18) |
| 40 weeks CA | 49.6 ± 3.1 (18) | 46.2 ± 2.3 (17) | 49.4 ± 3.2 (17) |
| 4 months CA | 130.5 ± 6.4 (15) | 136.4 ± 6.7 (12) | 132.2 ± 5.0 (12) |
| 12 months CA | 226.2 ± 10.5 (12) | 234.0 ± 7.4 (12) | 239.4 ± 10.3 (10) |
| LEAN BODY MASS (kg) | | | |
| 35 weeks CA | 1.67 ± 0.09 (17) | 1.72 ± 0.07 (18) | 1.75 ± 0.06 (18) |
| 40 weeks CA | 2.63 ± 0.08 (18) | 2.66 ± 0.08 (17) | 2.75 ± 0.11 (17) |
| 4 months CA | 4.48 ± 0.16 (15) | 4.75 ± 0.17 (12) | 4.55 ± 0.18 (12) |
| 12 months CA | 6.64 ± 0.23$^a$ (12) | 7.02 ± 0.20$^a$ (12) | 6.63 ± 0.17$^b$ (10) |
| FAT MASS (kg) | | | |
| 35 weeks CA | 0.27 ± 0.03 (17) | 0.25 ± 0.03 (18) | 0.23 ± 0.02 (18) |
| 40 weeks CA | 0.64 ± 0.07 (18) | 0.55 ± 0.04 (17) | 0.60 ± 0.05 (17) |
| 4 months CA | 1.86 ± 0.16 (15) | 1.95 ± 0.17 (12) | 2.09 ± 0.21 (12) |
| 12 months CA | 2.39 ± 0.18$^a$ (12) | 2.71 ± 0.18$^a$ (12) | 3.26 ± 0.26$^b$ (10) |

Data are reported as the unadjusted mean ± SEM (number of subjects)
Differences among groups were determined using repeated measures ANCOVA controlling for visit,

1.12 Conclusion

No differences in growth or bone mineralization between 35 wks and 12 mo CA were found in preterm infants fed an unsupplemented control formula and those fed formulas supplemented with 0.16 to 0.26 wt % DHA and 0.41 to 0.43 wt % ARA from combinations of either fungal and fish oils, or from egg-derived triglyceride and fish oil. The most significant finding was that supplementation with DHA and ARA at the levels studied led to increased lean body mass and reduced fat mass at 12 mo CA.

1.13 References (1) Carlson S E, Neuringer M. Polyunsaturated fatty acid status and neurodevelopment: a summary and critical analysis of the literature. *Lipids* 1999; 34:171-178.

(2) Innis S M. The role of dietary n-6 and n-3 fatty acids in the developing brain. *Dev Neurosci* 2000; 22:474-480.

(3) O'Connor D L, Hall R, Adamkin D, et al. Growth and development in preterm infants fed long-chain polyunsaturated fatty acids: a prospective, randomized controlled trial. *Pediatrics* 2001; 108:359-371.

(4) SanGiovanni J P, Berkey C S, Dwyer J T, Colditz G A. Dietary essential fatty acids, long-chain polyunsaturated fatty acids, and visual resolution acuity in healthy fullterm infants: a systematic review. *Early Hum Dev* 2000; 57:165-188.

(5) Innis S M, Adamkin D H, Hall R T, et al. Docosahexaenoic acid and arachidonic acid enhance growth with no adverse effects in preterm infants fed formula. *J Pediatr* 2002; 140:547-554.

(6) Morales-Martinez J J, Gonzalez-Pina R, Alfaro-Rodriguez A. Brainstem auditory response in the reserpinized rat *Proc West Pharmacol Soc* 2002; 45:68-70.

(7) Vanderhoof J, Gross S, Hegyi T. A multicenter long-term safety and efficacy trial of preterm formula supplemented with long-chain polyunsaturated fatty acids. *J Pediatr Gastroenterol Nutr* 2000,31:121-127.

(8) Fewtrell M S, Morley R, Abbott R A, et al. Double-blind, randomized trial of long-chain polyunsaturated fatty acid supplementation in formula fed to preterm infants. *Pediatrics* 2002; 1 10:73-82.

(9) Watkins B A, Lippman H E, Le Bouteiller L, et al. Bioactive fatty acids: role in bone biology and bone cell function. *Prog Lipid Res* 2001; 40:125-148.

(10) Peyron-Caso E, Quignard-Boulange A, Laromiguiere M, et al. Dietary fish oil increases lipid mobilization but does not decrease lipid storage-related enzyme activities in adipose tissue of insulin-resistant, sucrose-fed rats. *J Nutr* 2003; 133:2239-2243.

(11) Raclot T, Groscolas R, Langin D, Ferre P. Site-specific regulation of gene expression by n-3 polyunsaturated fatty acids in rat white adipose tissues. *J Lipid Res* 1997; 38:1963-1972.

(12) Raisz L G. Bone cell biology: new approaches and unanswered questions. *J Bone Miner Res* 1993; 8 Suppl 2:S457-S465.

(13) Watkins B A, Li Y, Lippman H E, Feng S. Modulatory effect of omega-3 polyunsaturated fatty acids on osteoblast function and bone metabolism. *Prostaglandins, Leukotrienes and Essential Fatty Acids* 2003; 68:387-398.

(14) Association for Official Agricultural Chemists. Official Methods of Analysis. 14 ed. Arlington, V A: Association for Official Agricultural Chemists, 1984.

(15) Ryan A S, Montalto M B, Groh-Wargo S, et al. Effect of DHA-containing formula on growth of preterm infants to 59 weeks postmenstrual age. *Am J Human Biol* 1999; 11:457-467.

(16) Carver J D, Wu P Y, Hall R T, et al. Growth of preterm infants fed nutrient-enriched or term formula after hospital discharge. *Pediatrics* 2001; 107:683-689.

(17) Cooke R J, Embleton N D, Griffin I J, et al. Feeding preterm infants after hospital discharge: growth and development at 18 months of age. *Pediatr Res* 2001; 49:719-722.

(18) Lucas A, Fewtrell M S, Morley R, et al. Randomized trial of nutrient-enriched formula versus standard formula for postdischarge preterm infants. *Pediatrics* 2001; 108:703-711.

(19) Worrell L A, Thorp J W, Tucker R, et al. The effects of the introduction of a high-nutrient transitional formula on growth and development of very-low-birth-weight infants. *J Perinatol* 2002; 22:112-119.

(20) Rajaram S, Carlson S E, Koo W W, Braselton W E. Plasma mineral concentrations in preterm infants fed a nutrient-enriched formula after hospital discharge. *J Pediatr* 1995; 126:791-796.

(21) Bishop N J, King F J, Lucas A. Increased bone mineral content of preterm infants fed with a nutrient enriched formula after discharge from hospital. *Arch Dis Child* 1993; 68:573-578.

(22) Chan G M. Growth and bone mineral status of discharged very low birth weight infants fed different formulas or human milk. *The Journal of Pediatrics* 1993; 123: 439-443.

(23) Cooke R J, McCormick K, Griffin I J, et al. Feeding preterm infants after hospital discharge: effect of diet on body composition. *Pediatr Res* 1999; 46:461-464.

(24) De Curtis M, Pieltain C, Rigo. J. Body composition in preterm infants fed standard term or enriched formula after hospital discharge. *Eur J Nutr* 2002; 41:177-182.

(25) Reichman B, Chessex P, Putet G, et al. Diet, fat accretion, and growth in premature infants. *N Engl J Med* 1981; 305:1495-1500.

(26) Wauben I P, Atkinson S A, Shah J K, Paes B. Growth and body composition of preterm infants: influence of nutrient fortification of mother's milk in hospital and breastfeeding post-hospital discharge. *Acta Paediatr* 1998; 87:780-785.

(27) Schmeizle H R, Fusch C. Body fat in neonates and young infants: validation of skinfold thickness versus dual-energy X-ray absorptiometry. *American Journal of Clinical Nutrition* 2002; 76:1096-1100.

(28) Raclot T, Oudart H. Selectivity of fatty acids on lipid metabolism and gene expression. *Proc Nutr Soc* 1999; 58:633-646.

(29) Hill J O, Peters J C, Lin D, et al. Lipid accumulation and body fat distribution is influenced by type of dietary fat fed to rats. *Int J Obes Relat Metab Disord* 1993; 17:223-236.

(30) Parrish C C, Pathy D A, Angel A. Dietary fish oils limit adipose tissue hypertophy in rats. *Metabolism* 1990; 39:217-219.

(31) Petersen R K, Jorgensen C, Rustan A C, et al. Arachidonic acid-dependent inhibition of adipocyte differentiation requires PKA activity and is associated with sustained expression of cyclooxygenases. *J Lipid Res* 2003;

(32) Benhizia F, Hainault I, Serougne C, et al. Effects of a fish oil-lard diet on rat plasma lipoproteins, liver FAS, and lipolytic enzymes. *Am J Physiol* 1994; 267:E975-E982.

(33) Halvorsen B, Rustan A C, Madsen L, et al. Effects of long-chain monounsaturated and n-3 fatty acids on fatty acid oxidation and lipid composition in rats. *Ann Nutr Metab* 2001; 45:30-37.

(34) Rustan A C, Hustvedt B E, Drevon C A. Postprandial decrease in plasma unesterified fatty acids during n-3 fatty acid feeding is not caused by accumulation of fatty acids in adipose tissue. *Biochim Biophys Acta* 1998; 1390:245-257.

(35) Peyron-Caso E, Tavema M, Guerre-Millo M, et al. Dietary (n-3) polyunsaturated fatty acids up-regulate plasma leptin in insulin-resistant rats. *J Nutr* 2002; 132: 2235-2240.

(36) Clandinin M T, Van Aerde J E, Parrott A, et al. Assessment of the efficacious dose of arachidonic and docosahexaenoic acids in preterm infant formulas: fatty acid composition of erythrocyte membrane lipids. *Pediatr Res* 1997; 42:819-825.

(37) Faldella G, Govoni A, Alessandroni R, et al. Visual evoked potentials and dietary long chain polyunsaturated fatty acids in preterm infants. *Arch Dis Child Fetal Neonatal Ed* 1996; 75:F108-F112.

(38) Vanderhoof J, Gross S, Hegyi T, et al. Evaluation of a long-chain polyunsaturated fatty acid supplemented formula on growth, tolerance, and plasma lipids in preterm infants up to 48 weeks postconceptional age. *J Pediatr Gastroenterol Nutr* 1999; 29:318-326.
(39) Lapillonne A, Braillon P, Claris O, et al. Body composition in appropriate and in small for gestational age infants. *Acta Paediatr* 1997; 86:196-200.
(40) Hediger M L, Overpeck M D, Kuczmarski R J, et al. Muscularity and fatness of infants and young children born small- or large-for-gestational-age. *Pediatrics* 1998; 102: E60.
(41) Barker D J. Intrauterine programming of coronary heart disease and stroke. *Acta Paediatr Suppl* 1997; 423:178-182.
(42) Barker D L. The fetal origins of coronary heart disease. *Acta Paediatr Suppl* 1997; 422:78-82.
(43) Phipps K, Barker D J, Hales C N, et al. Fetal growth and impaired glucose tolerance in men and women. *Diabetologia* 1993; 36:225-228.
(44) Eriksson J G, Forsen T, Tuomilehto J, et al. Early growth and coronary heart disease in later life: longitudinal study. *BMJ* 2001; 322:949-953.
(45) Ehrenkranz R A, Younes N, Lemons J A, et al. Longitudinal growth of hospitalized very low birth weight infants. *Pediatrics* 1999; 104:280-289.
(46) Lemons J A, Bauer C R, Oh W, et al. Very low birth weight outcomes of the National Institute of Child health and human development neonatal research network, January 1995 through December 1996. NICHD Neonatal Research Network. *Pediatrics* 2001; 107:E1.
(47) Casey P H, Kraemer H C, Bembaum J, et al. Growth status and growth rates of a varied sample of low birth weight, preterm infants: a longitudinal cohort from birth to three years of age. *J Pediatr* 1991; 119:599-605.
(48) Watkins B A, Li Y, Allen K G, et al. Dietary ratio of (n-6)/(n-3) polyunsaturated fatty acids alters the fatty acid composition of bone compartments and biomarkers of bone formation in rats. *J Nutr* 2000; 130:2274-2284.
(49) Sirois I, Cheung A M, Ward W E. Biomechanical bone strength and bone mass in young male and female rats fed a fish oil diet. *Prostaglandins Leukot Essent Fatty Acids* 2003; 68:415-421.
(50) Lucia V D, Fitzpatrick-Wong S C, Weiler H A. Dietary arachidonic acid suppresses bone turnover in contrast to low dosage exogenous prostaglandin E2 that elevates bone formation in the piglet. *Prostaglaidins, Leuktrienes and Essential Fatty Acids* 2003; 68:407-413.
(51) Weiler H A. Dietary supplementation of arachidonic acid is associated with higher whole body weight and bone mineral density in growing pigs. *Pediatr Res* 2000; 47:692-697.
(52) Watkins B A, Shen C L, McMurtry J P, et al. Dietary lipids modulate bone prostaglandin E2 production, insulin-like growth factor-I concentration and formation rate in chicks. *J Nutr* 1997; 127:1084-1091.
(53) Weiler H A, Fitzpatrick-Wong S. Dietary long-chain polyunsaturated fatty acids minimize dexamethasone-induced reductions in arachidonic acid status but not bone mineral content in piglets. *Pediatr Res* 2002; 51:282-289.
(54) Watkins B A, Shen C L, Allen K G, Seifert M F. Dietary (n-3) and (n-6) polyunsaturates and acetylsalicylic acid alter ex vivo PGE2 biosynthesis, tissue IGF-I levels, and bone morphometry in chicks. *J Bone Miner Res* 1996; 11:1321-1332.
(55) Rigo J, De Curtis M, Pieltain C, et al. Bone mineral metabolism in the micropremie. *Clin Perinatol* 2000; 27:147-170.
(56) Carlson S E, Cooke R J, Werkman, S I Tolley E A. First year growth of preterm infants fed standard compared to marine oil n-3 supplemented formula; *Lipids* 1992; 27:901-907.
(57) Carlson S E, Werkman S H, Tolley E A. Effect of long-chain n-3 fatty acid supplementation on visual acuity and growth of preterm infants with and without bronchopulmonary dysplasia *Am J Clin Nutr* 1996; 63:687-697.

What is claimed is:

1. A method of increasing lean body mass and reducing fat body mass in preterm infants, said method comprising:
   feeding the preterm infant in need of such treatment a nutritional formula comprising DHA and ARA from fish and fungal oil, wherein the DHA is present in an amount from 0.1 to 0.3% by weight of fat, and the ARA is present in an amount from 0.4 to 0.5% by weight of fat; and
   evaluating the lean body mass and fat body mass of the preterm infant after feeding the preterm infant the nutritional formula.

2. The method of claim 1 wherein the fat body mass of the preterm infant is reduced by at least about 15% at 12 months corrected age as compared to preterm infants fed the control nutritional formula.

3. A method of increasing lean body mass and reducing fat body mass in preterm infants, said method comprising feeding the preterm infant in need of such treatment a nutritional formula comprising DHA and ARA from egg-derived triglyceride and fish oil, wherein the DHA is present in an amount from 0.1 to 0.3% by weight of fat, and the ARA is present in an amount from 0.4 to 0.5% by weight of fat; and
   evaluating the lean body mass and fat body mass of the preterm infant after feeding the preterm infant the nutritional formula.

4. The method of claim 3 wherein the fat body mass of the preterm infant is reduced by at least about 15% at 12 months corrected age as compared to preterm infants fed the control nutritional formula.

5. A method of increasing lean body mass and reducing fat body mass in preterm infants, said method comprising feeding the preterm infant in need of such treatment a nutritional formula comprising a source of DHA and ARA selected from the group consisting of fungal oil, egg-derived triglyceride, fish oil, and combinations thereof, wherein the DHA is present in an amount from 0.1 to 0.3% by weight of fat, and the ARA is present in an amount from 0.4 to 0.5% by weight of fat; and
   evaluating the lean body mass and fat body mass of the preterm infant after feeding the preterm infant the nutritional formula.

6. A method of increasing lean body mass and reducing fat body mass in infants, said method comprising:
   feeding the infant in need of such treatment a nutritional formula comprising a source of DHA and ARA, wherein the DHA is present in an amount from 0.1 to 0.3% by weight of fat, and the ARA is present in an amount from 0.4 to 0.5% by weight of fat; and
evaluating the lean body mass and fat body mass of the infant after feeding the infant the nutritional formula.

7. The method of claim 6, wherein the feeding provides the infant with an average daily intake per kg body weight of from about 2 to about 65 mg DHA and from about 2 to about 65 mg ARA.

8. The method of claim 6, wherein the feeding provides the infant with an average daily intake per kg body weight of from about 3 to about 35 mg DHA and from about 5 to about 50 mg ARA.

9. The method of claim 6, wherein the feeding provides the infant with an average daily intake per kg body weight of from about 7 to about 26 mg DHA and from about 20 to about 40 mg ARA.

10. The method of claim 6, wherein the daily feeding is applied to infants that are less than about 1 year corrected age.

11. The method of claim 6, wherein the nutritional formula further comprises protein, lipid and carbohydrate.

12. The method of claim 6, wherein the nutritional formula provides a caloric density of from about 19 kcal/fl oz to about 24 kcal/fl oz.

13. The method of claim 6, wherein the nutritional formula comprises per each 100 kcal of said formula:
   (A) from about 3 grams to about 8 grams of lipid;
   (B) from about 1 gram to about 3.5 grams of protein; and
   (C) from about 8 grams to about 16 grams of carbohydrate.

14. The method of claim 6, wherein the nutritional formula comprises per each 100 kcal of said formula:
   (A) from about 4 grams to about 6.6 grams of lipid;
   (B) from about 1.5 gram to about 3.4 grams of protein; and
   (C) from about 9 grams to about 13 grams of carbohydrate.

* * * * *